US00PP32726P2

(12) United States Plant Patent
von Tubeuf

(10) Patent No.: US PP32,726 P2
(45) Date of Patent: Jan. 5, 2021

(54) POINSETTIA PLANT NAMED 'NPCW19282'

(50) Latin Name: *Euphorbia pulcherrima*
Varietal Denomination: NPCW19282

(71) Applicant: Klemm+Sohn GmbH & Co. KG, Stuttgart (DE)

(72) Inventor: Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/873,129

(22) Filed: Feb. 6, 2020

(51) Int. Cl.
*A01H 6/38* (2018.01)
*A01H 5/02* (2018.01)

(52) U.S. Cl.
USPC ..... Plt./307

(58) Field of Classification Search
USPC ..... Plt./307
CPC ..... A01H 6/38; A01H 5/02
See application file for complete search history.

*Primary Examiner* — Annette H Para
(74) *Attorney, Agent, or Firm* — Weatherly IP Solutions, LLC; Barbara Campbell

(57) ABSTRACT

A new poinsettia plant particularly distinguished by having red bracts having an upright habit, and having a triangular plant form, is disclosed.

1 Drawing Sheet

Genus and species: *Euphorbia pulcherrima.*
Variety denomination: 'NPCW19282'.

BACKGROUND OF THE NEW PLANT

The present invention comprises a new and distinct variety of poinsettia, botanically known as *Euphorbia pulcherrima* and hereinafter referred to by the variety name 'NPCW19282'. 'NPCW19282' was derived from a cross conducted indoors in a greenhouse in Juja, Kenya in December 2013 between the female poinsettia 'Prima Red', also known as 'Dueprima' (U.S. Plant Pat. No. 25,480) and the male poinsettia 'CHRISTMAS BEAUTY Red', also known as 'NPCW10158' (U.S. Plant Pat. No. 22,580).

Seedlings from the cross were subsequently planted and in August 2014, a single plant was selected in Stuttgart, Germany. In February 2015, 'NPCW19282' was first asexually propagated by vegetative apical cuttings in Stuttgart, Germany. 'NPCW19282' was found to reproduce true to type in successive generations of asexual propagation via vegetative apical cuttings in Stuttgart, Germany.

SUMMARY

The following are the most outstanding and distinguishing characteristics of this new variety when grown under normal horticultural practices in Stuttgart, Germany.

1. Red bracts having an upright habit; and
2. Having a triangular plant form.

DESCRIPTION OF THE PHOTOGRAPH

This new poinsettia plant is illustrated by the accompanying photograph which shows an overall view of the whole plant. The photograph is of a plant approximately 12 weeks old grown indoors in Stuttgart, Germany in December 2017. The colors shown are as true as can be reasonably obtained by conventional photographic procedures.

DESCRIPTION OF THE NEW VARIETY

The following detailed descriptions set forth the distinctive characteristics of 'NPCW19282'. The data which define these characteristics were collected from asexual reproductions carried out in Stuttgart, Germany. Data was collected on plants that were 4-months-old and grown in a glass greenhouse under normal horticultural practices in Stuttgart, Germany in November 2019. Color references are to The R.H.S. Colour Chart of The Royal Horticultural Society of London (R.H.S.), 5$^{th}$ edition (2007) unless where otherwise stated.

Classification:
- *Family.*—Euphorbiaceae.
- *Species.*—*Euphorbia pulcherrima.*
- *Common name.*—Poinsettia.
- *Variety.*—'NPCW19282'.

Parentage:
- *Female.*—'Prima Red', also known as 'Dueprima' (U.S. Plant Pat. No. 25,480).
- *Male.*—CHRISTMAS BEAUTY 'Red', also known as 'NPCW10158' (U.S. Plant Pat. No. 22,580).

Plant:
- *Form.*—Triangular.
- *Growth habit.*—Upright.
- *Height.*—19 cm to 21 cm.
- *Width.*—29 cm to 31 cm.
- *Average number of inflorescences per plant.*—5 to 6.
- *Keeping quality.*—Very good.
- *Time to produce a cutting.*—5 to 6 weeks.
- *Flowering response time.*—Approximately 55 days.
- *Propagation type.*—Apical cuttings.
- *Rooting habit and root color.*—Freely branching and white.

Lateral branches:
- *Color.*—RHS 143A (Green).
- *Length.*—16 cm to 20 cm.
- *Internode length.*—0.5 cm to 3.0 cm.
- *Diameter.*—0.4 cm to 0.6 cm.
- *Branching habit.*—Freely branching.
- *Number of lateral branches per plant.*—6 to 7.
- *Texture.*—Smooth.
- *Strength.*—Sturdy.

Leaves:

*Quantity.*—6 to 8 per lateral branch.

*Arrangement.*—Alternate.

*Number of lobes on the leaf blade.*—1 to 2.

*Lobation depth.*—Almost absent, most leaves have almost entire margins.

*Depth of the deepest sinus of the leaf blade.*—0.2 cm.

*Shape.*—Obtuse.

*Apex.*—Acuminate.

*Base.*—Rounded.

*Margin.*—Some margins are serrate but most are entire.

*Length.*—6 cm to 8 cm.

*Width.*—6 cm to 8 cm.

*Texture (both upper and lower surfaces).*—Smooth.

*Vein color.*—Upper surface: No color; transparent. Lower surface: RHS 139D and main vein is slightly reddish, close to RHS 184 C.

*Variegation.*—Absent.

*Venation pattern.*—Reticulate.

*Color.*—Mature foliage: Upper surface: RHS 139A (Green). Lower surface: RHS 139D (Green). Immature foliage: Upper surface: RHS 141A (Green). Lower surface: RHS 139B (Green).

*Leaf petiole.*—Length: 3 cm to 4 cm. Diameter: 0.2 cm to 0.3 cm. Color: Upper (part) surface: RHS 59A (Red-Purple). Lower (part) surface: RHS 181B (Greyed-Red). Texture: Smooth. Strength: Medium.

*Transitional leaves.*—Few; shape is ovate, length is 4.0 cm to 8.0 cm, width is 3.0 cm to 6.0 cm and color of the upper surface is RHS 46A and regions close to RHS N186B and lower surface is RHS 138B and regions close to RHS 46B.

Inflorescence:

*Type and habit.*—Cluster of cyathia.

*Quantity per lateral branch.*—1

*Position relative to foliar plane.*—Above.

*Lastingness of inflorescence on the plant.*—4 to 5 weeks.

*Natural flowering season.*—End of November.

*Diameter.*—16 cm to 18 cm.

*Height.*—2 cm to 3 cm.

*Fragrance.*—Absent.

Bracts:

*Number of bracts per inflorescence.*—8 to 10.

*Shape.*—Ovate.

*Apex.*—Obtuse.

*Base.*—Rounded.

*Margin.*—Entire.

*Size.*—Length: 5 cm to 11 cm. Width: 4 cm to 7 cm.

*Texture (both upper and lower surfaces).*—Smooth.

*Folding along the main vein.*—Absent.

*Twisting.*—Absent.

*Rugosity between the veins.*—Medium.

*Venation pattern.*—Reticulate.

*Vein color.*—Upper surface: RHS 59A (Red-Purple). Lower surface: RHS 181B (Greyed-Red).

*Bract color.*—Upper surface: Close to RHS 46B (Red). Lower surface: Close to RHS 45B (Red).

*Bract petiole.*—Length: 0.5 cm to 1.5 cm. Diameter: 0.2 cm. Color: Upper (part) surface: RHS 59A (Red-Purple). Lower (part) surface: RHS 181A (Greyed-Purple). Texture: Smooth. Strength: Medium.

Cyme:

*Diameter.*—1.5 cm to 2.5 cm.

*Cyathia number.*—5 to 7 per inflorescence.

*Deformation of glands of the cyathium.*—Absent.

*Timing of opening of cyathia.*—Opens end of November; first pollen appears in parallel to opening of the nectar cups, stigmas arrive 2 weeks later.

*Cyathium.*—Shape: Ovate. Texture (inner and outer surfaces): Smooth. Diameter: 0.2 cm to 0.5 cm. Length: 0.3 cm to 0.7 cm. Color: RHS 143C (Green).

*Peduncle.*—Color: RHS 142B (Green). Length: 0.2 cm. Diameter: 0.1 cm. Texture: Smooth. Strength: Medium.

*Nectar cups.*—Number: 1 per cyathium. Diameter: 0.1 cm. Length: 0.3 cm to 0.4 cm. Color: RHS 13A (Yellow). Shape: Lip-shaped. Texture (inner and outer surfaces): Smooth.

Reproductive organs:

*Stamen quantity.*—5 to 10 per cyathium.

*Stamen shape.*—Ovate.

*Filament length.*—0.25 cm.

*Filament color.*—RHS 46A (Red).

*Pollen quantity.*—Moderate to abundant.

*Pollen color.*—RHS 12A (Yellow).

*Gynoecium.*—Present. Pistil quantity per cyathium: 1. Pistil length: 0.2 cm. Stigma form: Divided in 2 parts. Stigma color: RHS 183A (Greyed-Purple). Style length 0.2 cm. Style color: RHS 183A (Greyed-Purple). Ovary length: 0.2 cm. Ovary color: RHS 143C (Green).

Fruit and seed set: None observed.

Disease and pest resistance: None observed.

COMPARISON WITH PARENTAL AND COMMERCIAL LINES

When 'NPCW19282' is compared to its parental lines, the following differences are noted in Table 1.

TABLE 1

| Characteristic | 'NPCW19282' | 'Prima Red' | CHRISTMAS BEAUTY 'Red' |
|---|---|---|---|
| Vigor | Medium | Medium to strong | Medium |
| Habit | Medium angle (upright) | Small angle (narrow and very upright) | Medium angle (upright) |
| Bract shape | More upright than CHRISTMAS BEAUTY | Horizontal | Less upright than 'NPCW19282' |

When 'NPCW19282' is compared to the commercial line 'NPCW15235' (U.S. Plant Pat. No. 28,703, the following differences are noted in Table 2.

TABLE 2

| Characteristic | 'NPCW19282' | 'NPCW15235' |
|---|---|---|
| Height | 19 cm to 21 cm | 22 cm to 27 cm |
| Lobation depth | Almost absent, most leaves have almost entire margins | Moderately deep |

I claim:

1. A new and distinct variety of poinsettia plant designated 'NPCW19282' as illustrated and described herein.

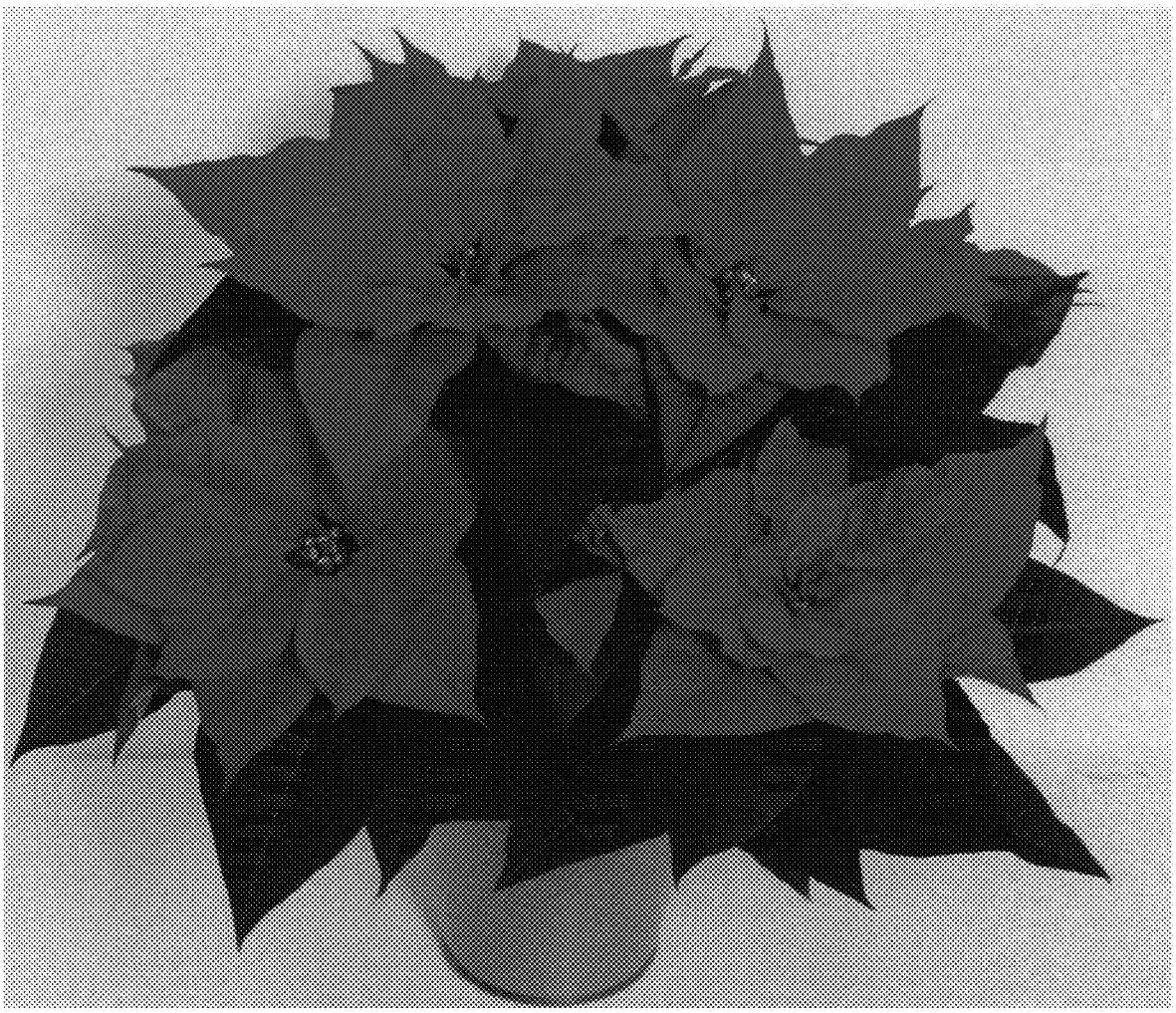

* * * * *